United States Patent [19]

Griebel et al.

[11] Patent Number: 5,340,226
[45] Date of Patent: Aug. 23, 1994

[54] PROCESS FOR THE PRODUCTION OF A PENCIL STICK, A STICK PRODUCED BY THE PROCESS AND A PENCIL HAVING SUCH A STICK

[75] Inventors: Ulrich Griebel, Altdorf; Claudia Kraska; Peter Schielein, both of Nuernberg, all of Fed. Rep. of Germany

[73] Assignee: Schwan-Stabilo Schwanhäusser GmbH & Co., Nuernberg, Fed. Rep. of Germany

[21] Appl. No.: 64,452

[22] Filed: May 21, 1993

[30] Foreign Application Priority Data

Feb. 22, 1993 [DE] Fed. Rep. of Germany ....... 4305369

[51] Int. Cl.⁵ .................................................. B43K 19/00
[52] U.S. Cl. ............................................ 401/96; 401/49
[58] Field of Search ............... 401/49, 88, 96, 97, 401/98; 152/320

[56] References Cited

U.S. PATENT DOCUMENTS

| 588,867 | 8/1897 | Knight | 401/49 |
|---|---|---|---|
| 1,595,948 | 8/1926 | King | 401/96 X |
| 2,231,410 | 2/1941 | Kern et al. | 401/96 |
| 3,453,056 | 7/1969 | Motsavage | 401/88 |
| 4,413,921 | 11/1983 | Fotiu et al. | 401/49 X |
| 4,545,983 | 10/1985 | Russ et al. | 49/88 X |

FOREIGN PATENT DOCUMENTS

| 2718957 | 11/1978 | Fed. Rep. of Germany . | |
| 2759610 | 11/1978 | Fed. Rep. of Germany . | |
| 2759856 | 11/1978 | Fed. Rep. of Germany . | |
| 3835680 | 4/1990 | Fed. Rep. of Germany . | |
| 4003288 | 8/1991 | Fed. Rep. of Germany . | |
| 4003289 | 8/1991 | Fed. Rep. of Germany . | |
| 972698 | 2/1951 | France | 401/96 |
| 141458 | 4/1920 | United Kingdom | 401/88 |
| 276512 | 9/1927 | United Kingdom | 401/96 |
| 2081579 | 7/1980 | United Kingdom | 401/49 |
| 2084084 | 4/1982 | United Kingdom | 401/49 |

*Primary Examiner*—Danton D. DeMille
*Attorney, Agent, or Firm*—Bachman & LaPointe

[57] ABSTRACT

In a process for the production of a pencil stick, a pencil stick produced by the process and a pencil having such a stick, a stick material is introduced into a thin-wall tube portion forming a mold, from one end thereof, the tube portion comprising a sharpenable plastic material.

9 Claims, 1 Drawing Sheet

PROCESS FOR THE PRODUCTION OF A PENCIL STICK, A STICK PRODUCED BY THE PROCESS AND A PENCIL HAVING SUCH A STICK

BACKGROUND OF THE INVENTION

Pencils and more especially cosmetic pencils are frequently produced either by a procedure in which a suitable cosmetic stick or lead material is extruded cold and glued into a grooved board portion using the method known from the manufacture of lead pencils, whereupon the board portion can be cut up lengthwise to form the finished pencils, or a procedure in which pourable cosmetic material is poured in a hot condition into prefabricated sleeve-like casing portions with a concentric hole therein, the stick material then being allowed to cool and harden in the casing portion.

In the first-mentioned extrusion procedure, it is only possible to use stick materials which result in relatively hard sticks as the sticks must remain handleable for further processing thereof. However, in relation to sticks for cosmetic pencils, that aspect involves a restriction in terms of the choice of extrudable textures, or it results in the pencil providing a relatively hard marking effect which is not desirable in cosmetic uses.

The above-mentioned pouring process on the other hand involves the problem that the process must use sleeve-shaped casing portions which are in a completely finished condition, that is to say which have been completely put into the desired shape and decorated. It will be appreciated that, in the event of such a pencil being rejected as defective, the processing costs involved in producing the casing portion in its completed form represent a considerable loss which thus has a major effect on overall production costs. Furthermore, when using casing portions comprising wood, wood substitutes or plastic material, roughness at the inside surface of the central hole in the casing portion result in the formation of gas bubbles when a hot cosmetic stick material is poured into the casing portion, due to the interaction between the hot cosmetic material and the material of the casing portion. The gas bubbles give rise in the finished stick to cavities which result in a reduction in the quality of the pencil such that in extreme cases the pencil has to be rejected and is thus a production loss. It is further possible that, in the liquefied condition of the stick material, components of that material may be absorbed by the material of the casing portion, and that can again result in a reduction in the quality of the stick material.

If cosmetic stick materials with volatile components such as for example volatile silicones, paraffins or the like are poured into casing portions of wood or wood substitutes, the inside surface of the hole of the casing portion has to be suitably coated or sealed off in order to prevent the volatile components from migrating or diffusing into the casing portion, as they would in turn result in undesirable changes in the quality of the pencil stick produced. For that reason it has not hitherto been readily possible to produce cosmetic pencils containing volatile components such as silicone oils, paraffins or the like, and to put them into intermediate storage over a prolonged period because the volatile components, in the storage situation, evaporate uncontrollably out of the stick materials, thus further resulting in an undesirable variation in the quality of the stick.

One form of a process for the production of a pencil stick, as is disclosed in DE 38 35 680 A1, involves using a mold comprising a plastic material, which is open in a slit-like configuration along at least a part of its peripheral surface. The mold preferably has a longitudinal slit extending over the entire length of the mold. Although it is possible in that way to introduce a stick material through the slit, the slitted open shape however means that it is not possible to prevent volatile components of the stick material evaporating uncontrollably out of same, particularly in a prolonged intermediate storage situation, and that once again, as indicated above, can result in an undesirable change in the quality of the stick.

The pencil which is intended in particular for cosmetic purposes and which has a stick produced by a casting procedure and which is firmly enclosed and held in position by a sharpenable casing portion of wood, as disclosed in DE 27 18 957 C3, provides that the casing portion of wood is in the form of a one-piece tubular member whose inside surface has a coating thereon, which acts as a barrier to prevent components of the stick material from penetrating into the casing portion. The stick material is poured into the tubular casing portion, forming an exposed tip for the pencil stick.

Another cosmetic pencil, as disclosed in DE 27 59 610 C2, has a pencil stick which is produced by a pouring process and a casing portion formed by a tubular member. The casing portion firmly embraces the stick, while both the casing portion and the stick can be sharpened to a point. The exposed tip of the pencil stick has a conical surface while the end of the casing portion is frustoconical so as to be in flush adjoining relationship with the conical surface of the exposed tip of the stick. The casing portion is a seamless plastic member into which the stick material is poured, forming the exposed tip thereof. The conical surface of the pencil tip and also a rounded-off end on the tip are formed when the stick material is poured into the casing portion. The inside surface of the casing portion may again be provided with a coating to prevent stick material or components thereof from diffusing into the casing portion. A similar form of cosmetic pencil is also to be found in DE 27 59 856 C2.

A writing pencil or crayon, as disclosed in DE 40 03 288 A1, comprises a sheathing and a stick disposed therein, the sheathing entirely or predominantly consisting of papier-maché, wood dust and/or mechanical wood pulp. DE 40 03 289 A1 discloses a writing pencil or crayon having a casing portion consisting of a sheathing of layers of paper, wood or plastic material, in sheet or foil form, and a lead or stick disposed therein, or another writing agent and/or writing agent storage device, and possibly a clamping device for holding the lead or stick and/or a feed device for advancing the lead or stick and/or other components. As indicated above, the sheathing which forms the casing portion entirely or predominantly consists of layers of paper, wood and/or plastic material in sheet or foil form, which are laminated one over the other or which are rolled together. However that pencil cannot be employed for cosmetic purposes.

SUMMARY OF THE INVENTION

An object of the present invention is to provide a process for the production of a stick for a pencil such as a cosmetic pencil, which permits prolonged intermediate storage of the stick and easy handling thereof without undesirable evaporation of a volatile component of the stick material or migration and/or diffusion which would result in a variation in the quality of the stick.

Another object of the present invention is to provide a stick for a pencil such as a cosmetic pencil, which can be manufactured in a readily operable fashion.

Still another object of the present invention is to provide a stick for a pencil, which permits prolonged intermediate storage thereof without involving unacceptable evaporation or migration or diffusion of a volatile constituent.

A further object of the present invention is to provide a pencil including a stick therein which reduces the risk of unacceptable evaporation of a volatile constituent of the stick material.

In accordance with the principles of the present invention, in a first aspect of the invention, the foregoing and other objects are achieved by a process for the production of a stick for a pencil such as a cosmetic pencil, wherein stick material is introduced into a mold. The mold is formed by a thin-wall tube portion which forms the space into which the stick material is suitably introduced, the tube portion comprising a sharpenable plastic material. The stick material is introduced into the tube portion from an end thereof.

In a preferred feature the stick material is poured or cast into the tube portion from one end thereof. It will be appreciated that it would likewise be possible for the stick material, in liquefied form, to be sucked into the tube portion, or for the pouring procedure and the suction procedure to be combined together, in such a way that the stick material is poured into the tube portion from one end thereof and at the same time a reduced pressure is applied to the other end of the tube portion. It would also be possible for the liquefied stick material to be introduced into the tube portion by means of a feed member such as a hollow needle or the like.

In another preferred feature the stick material can be extruded directly into the tube portion, preferably at elevated temperature.

In a desirable feature of the process of the invention, a hot liquefied stick material is poured into the tube portion. The stick material is advantageously poured into a tube portion which is closed at one end, for which purpose the tube portion of sharpenable plastic material may be welded at the appropriate end. It would likewise be possible for the tube portion to be closed off at one end by a suitable plug. The plug may comprise a suitable material such as plastic material, wax and the like.

In order to prevent undesirable evaporation of volatile components of the stick material out of the stick, a preferred feature of the process of the invention provides that the tube portion is closed off at the open end at which the stick material is poured into same, after the stick material has been poured in. The operation of closing off the end of the tube portion can be effected, like the operation of closing off the other end, for example by welding or by means of a plug of suitable material such as plastic material, wax or the like. In that respect welding has the advantage that it is very easy and quick to carry out, in comparison with inserting in particular a plastic plug.

In accordance with another feature of the invention, tube portions filled with the stick material can be fixed in a grooved board portion which is known per se from the production of lead pencils, and subjected to further processing in per se known fashion to provide finished pencils. That procedure preferably involves using board portions of wood or wood substitute.

It is however also possible for the tube portion to be disposed in a casing portion and for the stick material then to be introduced into the tube portion. The casing portion may comprise wood, a wood substitute or a plastic material. In that further form of the process, the thin-wall plastic tube portion is fitted to the casing portion and that assembly thus forms what can be referred to as a combination casing portion into which then the appropriate stick material is introduced, for example by being poured into same. It is also possible for the tube portion to be fitted into a suitable form of forward feed device such as a pushing device or rotational mechanism, and to sharpen the tube portion as required, as it is extended further out of that device.

In accordance with a preferred feature of the invention, for carrying out the last-mentioned form of the process using the above-defined combination casing portion, the tube portion may comprise a plastic material which softens when a hot liquefied stick material is poured into the tube portion, and bears snugly against the inside surface of the casing portion. That firm contact of the tube portion filled with stick material will reliably hold it in position to prevent it from falling out of the casing portion.

It will be appreciated that it is possible for the tube portion to be fixed in the grooved board portion in any other suitable fashion, for example by adhesive. On the one hand, that prevents the tube portion from dropping out of the finished casing portion, while on the other hand that prevents the tube portion from rotating in the sharpening operation.

An operation for closing the end of the tube portion, which is remote from the end at which the stick material is poured into the tube portion, by welding or by means of a plug, is unnecessary if the process is carried into effect using a casing portion which has a blind hole, in which the tube portion is disposed and then filled with the stick material. When carrying out that form of the process, it has been found desirable for the tube portion to be introduced into the casing portion only to such an extent that an end face of the tube portion, which is towards the bottom of the blind hole, is disposed at a spacing from the bottom of the blind hole so that the end face of the tube portion forms a retaining shoulder for the stick material. That secures the stick to prevent it from dropping out of the tube portion or the above-mentioned casing assembly consisting of the tube portion and the casing portion. For the same purpose, the process may involve the use of a tube portion which is provided at at least a part of its longitudinal extent with a reduced cross-section which differs from a round configuration, the tube portion being introduced into the casing portion before then the stick material is poured into the combination casing portion.

In accordance with a further aspect of the invention, the foregoing and other objects of the invention are attained by a stick for a pencil such as a cosmetic pencil which comprises stick material disposed in a mold formed by a thin-wall tube portion of a sharpenable plastic material. The stick material is closely surrounded by the tube portion so that there is a substantially reduced risk of undesirable or uncontrolled evaporation of volatile components of the stick material upon storage of the stick. That means however that there is a reduced risk of the quality of such a stick being adversely affected even after prolonged storage.

A preferred feature of the stick according to the invention provides that the tube portion which is filled with the stick material is sealingly closed off at least at one end and preferably at both ends.

In still another aspect of the invention, the foregoing and other objects are achieved by a pencil such as a cosmetic pencil having a casing portion containing a stick. The stick comprises stick material disposed in a thin-walled tube portion of a sharpenable plastic material which is fixed in the casing portion, the tube portion constituting a mold for the stick material which is introduced into same. The tube portion filled with the stick material can be closed off at at least one end and preferably it is sealingly closed off at its two ends.

The casing portion may comprise wood or a wood substitute or a plastic material.

The casing portion may have a through hole therein but the casing portion may have therein a blind hole in which the stick consisting of the stick material disposed in the thin-wall tube portion is fixed. The blind hole may for example have a parabolic bottom, whereby the movement for insertion of the tube portion into the casing portion is restricted in a defined manner. A similar consideration applies if the bottom of the blind hole is for example of a tapering configuration. Irrespective of the specific configuration of the inward end or bottom of the blind hole, it is advantageous for the tube portion to be spaced from the bottom of the blind hole so that the end face of the tube portion, which is towards the bottom of the blind hole, forms a holding shoulder for the stick material. That provides for reliable fixing of the cooled stick material in the tube portion after it has been poured into same while the fixing of the tube portion in the casing portion provides for suitable fixing of the stick or stick material in the casing portion. The tube portion can also be fixed in the casing portion by the tube portion being provided at at least a part of its longitudinal extent with a reduced cross-section which differs from a round configuration.

Due to shrinkage of a cast stick material, during cooling thereof, at the end portion at which the stick material is poured in, there may be formed a more or less severely pronounced concentric casting core portion which may weaken the structure of the stick at that end portion. If in accordance with the invention cosmetic sticks are produced in a two-stage procedure, that is to say firstly the sticks are produced and they are then glued into board portions, then, if the above-mentioned core portion is not too severely pronounced, the stick can be oriented with the core portion towards the inner closed end of the pencil, or alternatively the stick can be cast of greater length than is required for it to be glued in position and then cut to the required length, thereby removing the end portion containing the core portion.

Further objects, features and advantages of the present invention will be apparent from the following description.

DESCRIPTION OF PREFERRED EMBODIMENTS

Figure 1:
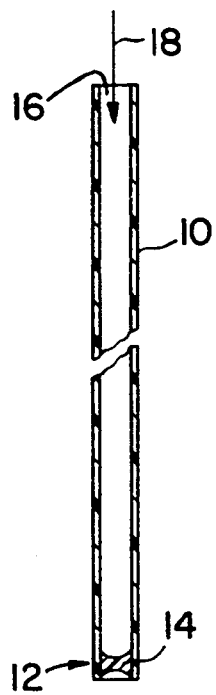
FIG. 1 is a view in longitudinal section of part of a thin-wall tube portion which is closed off at one end.

Referring firstly to FIG. 1, shown therein is a thin-wall tube portion 10 which comprises a sharpenable plastic material and which is intended for a stick of a pencil, more especially a cosmetic pencil. The tube portion 10 is sealed off at its one end portion 12 by means of a plug 14. The plug 14 may comprise any suitable material such as plastic material, wax or the like. The second end portion 16 of the thin-wall tube portion 10 is open in FIG. 1 so that the tube portion 10 can be filled with a stick material, such as a cosmetic stick material, through the open end portion 16. The filling step is indicated in FIG. 1 by means of the arrow 18. The cosmetic stick material is usually poured in a hot liquefied condition into the thin-wall tube portion 10 when it is disposed in an upright position.

Figure 2:
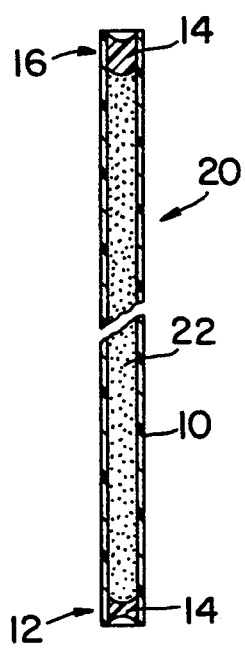
FIG. 2 is a sectional view similar to that shown in FIG. 1 of a thin-wall tube portion which is filled with a stick material and closed off at both ends.
Figure 3:
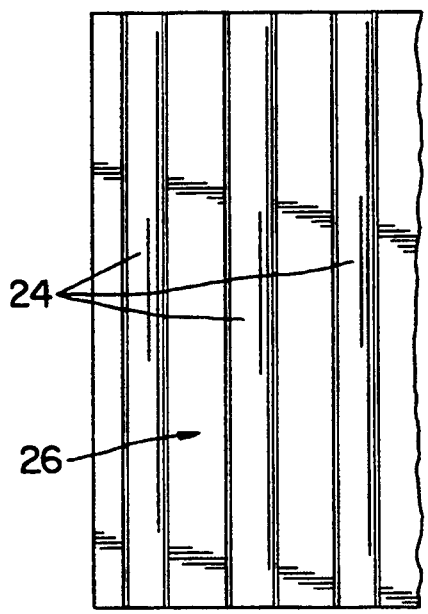
FIG. 3 shows a part of a grooved board portion for a number of sticks as shown in FIG. 2.

FIG. 2 shows a stick as generally indicated at 20, with a stick material 22 which has been poured into the thin-wall tube portion 10. The tube portion 10 is sealed off at the first end portion 12 and at the second end portion 16 by means of respective plugs 14 so that, even after prolonged intermediate storage of the stick 20, there are no major variations in quality due to the evaporation of volatile components of the stick material 22. The stick 20 can also be handled in a simple fashion without giving rise to serious problems, for example it can be fitted into a groove as indicated at 24 in FIG. 3 in a grooved board portion 26, or can be glued between two co-operating board portions 26 in a manner which is known per se from the production of lead pencils. FIG. 3 shows a plan view of part of such a board portion 26. The individual grooves 24 therein may be of semicircular cross-section or of a cross-section which differs from a semicircular configuration. It is possible for example for the grooves 24 to be of a flattened or oval cross-section in order to provide for a good clamping action to hold a tube portion 10 or a stick 20 therein.

Figure 4:
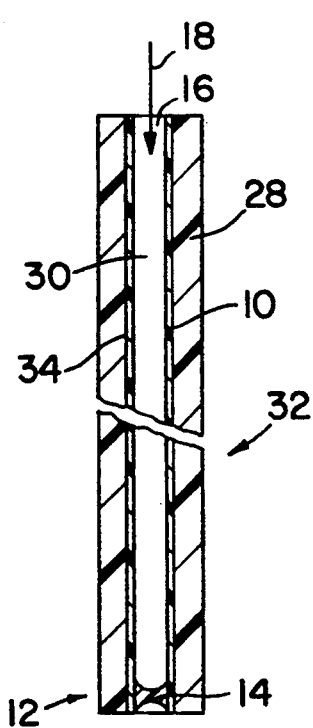
FIG. 4 is a view in longitudinal section of part of a casing portion having a thin-wall tube portion as shown in FIG. 1 arranged in its central hole.

Reference will now be made to FIG. 4 showing a view in longitudinal section of part of a casing portion 28 which has a central hole 30 passing therethrough. A thin-wall tube portion 10 of sharpenable plastic material is fixed in the hole 30. The tube portion 10 is sealingly closed at its lower end portion 12 by means of a plug 14 of suitable material. The second end portion 16 of the tube portion 10 is open so that a stick material, for example a cosmetic stick material, can be poured through the second open end portion 16 into the unit 32 consisting of the casing portion 28 and the tube portion 10, and thus into the interior of the tube portion 10, as is also indicated in FIG. 4 by the arrow 18. In this arrangement the tube portion 10 is preferably made of a plastic material which softens when the hot liquefied stick material is poured into same and bears snugly against the inside wall surface of the hole 30 in the casing portion 28, whereby the tube portion 10 which is filled with the stick material is prevented from falling out of the casing portion 28.

Figure 5:
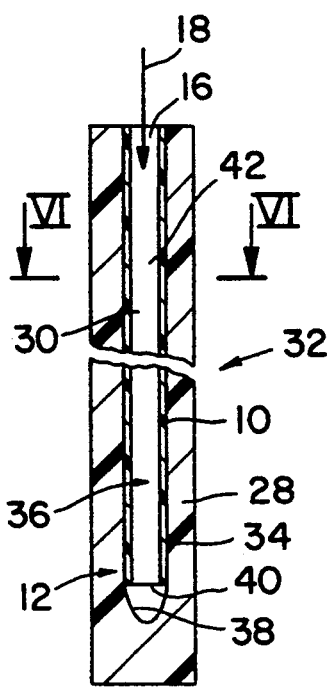
FIG. 5 is a view in section through a casing portion having a blind hole, in which a thin-wall tube portion is disposed.
Figure 6:
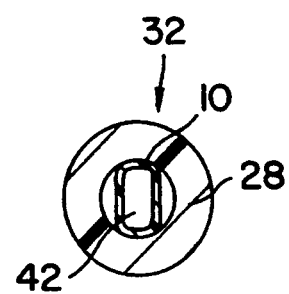
FIG. 6 is a view in section taken along section line VI—VI in FIG. 5 through a combination casing portion comprising a casing portion and a thin-wall tube portion arranged in its central hole.

FIG. 5 shows a combination casing unit 32 comprising a casing portion 28 and a thin-wall tube portion 10 disposed therein, the casing portion 28 having a central blind hole 36 for accommodating the tube portion 10. The blind hole 36 has a bottom as indicated at 38, which is of such a configuration that it preferably progressively decreases in width in a downward direction in FIG. 5. For example the blind hole 36 may have a bottom 38 of a parabolic configuration or a bottom 38 which tapers in a frustoconical configuration. That configuration provides that the movement for insertion of the tube portion 10 into the blind hole 36 is limited in a defined fashion in such a way that the annular end face 40 of the tube portion 10, which is towards the bottom 38 of the blind hole 36, is at a given spacing from the bottom 38 of the blind hole 36. When a hot liquefied stick material is poured into such a combination casing portion 32 from the open end portion 16 thereof, as indicated by the arrow 18, the above-mentioned annular end face 40 of the tube portion 10 forms a holding shoulder for the stick material, by virtue of which the stick material is fixed in position relative to the tube portion 10. For the same purpose, it may be appropriate to use a tube portion 10 which, as shown in FIG. 6, at least a part 42 of its longitudinal extent, is of a reduced cross-section which differs from a circular shape.

The length of the tube portion 10 may be as desired, that is to say it is suitably matched to the length of the blind hole 36. The end face 40 of the tube portion 10 does not have to extend as far as the reducing bottom 38 of the blind hole 36, for it may also be spaced therefrom without thereby having an adverse effect on fixing of the stick material in the tube portion.

It will be appreciated that the above-described processes for the production of a stick for a pencil such as a cosmetic pencil, a stick for a pencil, and the pencil itself, have been set forth solely by way of example and illustration of the principles of the present invention and that various modifications and alterations may be made therein without thereby departing from the spirit and scope of the invention.

We claim:

1. A process for the production of a pencil comprising the steps: disposing a thin-walled tube portion having first and second opposed open ends into a blind hole of a casing to provide said first open end adjacent said blind hole and said second open end as a free end thereof, pouring a hot liquified stick material within said second open end wherein the stick material solidifies in the tube portion, and wherein the tube portion is made from a sharpenable plastic material which softens when the hot stick material is poured into same and which bears snugly against the inside surface of the casing portion, including the step of introducing the tube portion into the casing portion only to such a degree that an end face of the tube portion which is towards the bottom of the blind hole is at a spacing from the bottom of the blind hole so that said end face of the tube portion forms a retaining shoulder for the stick material.

2. A process as set forth in claim 1 including the step of providing that the blind hole has a shape selected from the group consisting of parabolic and frustoconical.

3. A process as set forth in claim 1 including the step of providing the tube portion in at least a part of its longitudinal extent with a reduced cross-section which differs from a round configuration.

4. A process as set forth in claim 1 including the step of providing that said stick material is cosmetic material, for a cosmetic pencil.

5. A pencil comprising a casing portion which has a blind hole and an inside surface, a thin-wall tube portion of a sharpenable plastic material which softens when hot stick material is poured into same bearing snugly against the inside surface of the casing portion, wherein the tube portion is spaced from the bottom of the blind hole, said tube portion having an end face thereof which is towards the bottom of the blind hole, and a solidified stick material which has been poured into the tube portion, wherein the end face of the tube portion forms a retaining shoulder for the poured and solidified stick material.

6. A pencil as set forth in claim 5 wherein the casing portion comprises wood.

7. A pencil as set forth in claim 5 wherein the casing portion comprises a wood substitute.

8. A pencil as set forth in claim 5 wherein the tube portion is provided in at least a part of its longitudinal extent with a reduced cross-section which differs from a round configuration.

9. A pencil as set forth in claim 5 wherein the blind hold has a shape selected from the group consisting of parabolic and frustoconical.

* * * * *